United States Patent [19]

Melnyk

[11] 4,110,167
[45] Aug. 29, 1978

[54] SEMI-AUTOMATED SLIDE PROCESSOR DEVICE

[76] Inventor: John Melnyk, 1316 Cerritos Dr., Laguna Beach, Calif. 92651

[21] Appl. No.: 814,854

[22] Filed: Jul. 12, 1977

[51] Int. Cl.² .............................................. C12K 1/00
[52] U.S. Cl. .................................................... 195/127
[58] Field of Search ........................................ 195/127

[56] References Cited
U.S. PATENT DOCUMENTS 3,574,064   4/1971   Binnings et al. .................. 195/127

Primary Examiner—Alvin E. Tanenholtz
Attorney, Agent, or Firm—John Joseph Hall

[57] ABSTRACT

A semi-automated slide processor device for making slides of cell specimens from cell cultures within a single unit, having a slide feeding means, a cell dispenser means, a cell dispersal means, slide heating means, and means for collecting the finished slides in magazines.

6 Claims, 7 Drawing Figures

SEMI-AUTOMATED SLIDE PROCESSOR DEVICE

BACKGROUND OF THE INVENTION

This invention pertains to the field of devices for processing cell cultures onto slides for cytogenetic analysis, said slides being completed within a single housing unit.

SUMMARY OF THE INVENTION

The invention provides a device for rapid and reproducible preparation of slides of cell cultures. The device provides means for storing a supply of glass slides together with means for feeding a plurality of the slides simultaneously as desired through a cell dispenser assembly, where the slides receive the desired cell specimens. Cell dispersing means then spread the cell cultures on the slides into a thin film, while heating means simultaneously dries the film on the slides. after which the device collects the slides in magazines for storage.

This slide processor device makes possible the rapid production of a plurality of slides of cell cultures in a fraction of the time formerly required by other methods, as much as eight times faster.

It is, therefore, an object of this invention to provide rapid semi-automated means for simultaneously preparing a plurality of slides of cell cultures for cytogenetic analysis.

Another object of this invention is to provide rapid semi-automated means for preparing a plurality of slides of cell cultures for cytogenetic analysis, which means is contained in a single, relatively compact unit.

A further object of this invention is to provide means for processing a plurality of slides of cell cultures in a fraction of the time formerly required by other methods.

These and other objects will be more readily understood by reference to the following specification, taken in conjunction with the accompanying drawings, in which.

Figure 1:
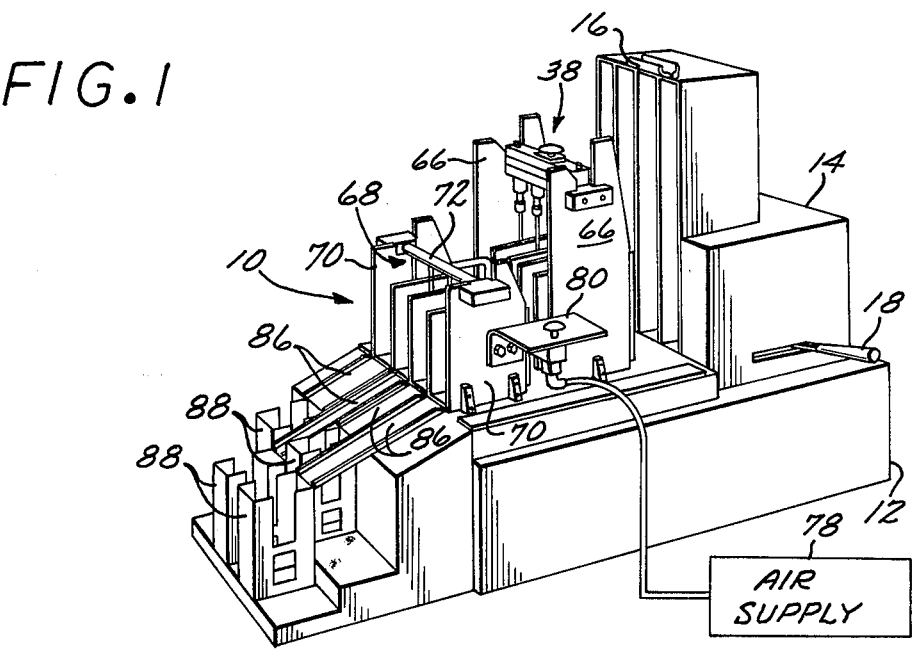
FIG. 1 is a perspective view of an embodiment of the invention.
Figure 2:
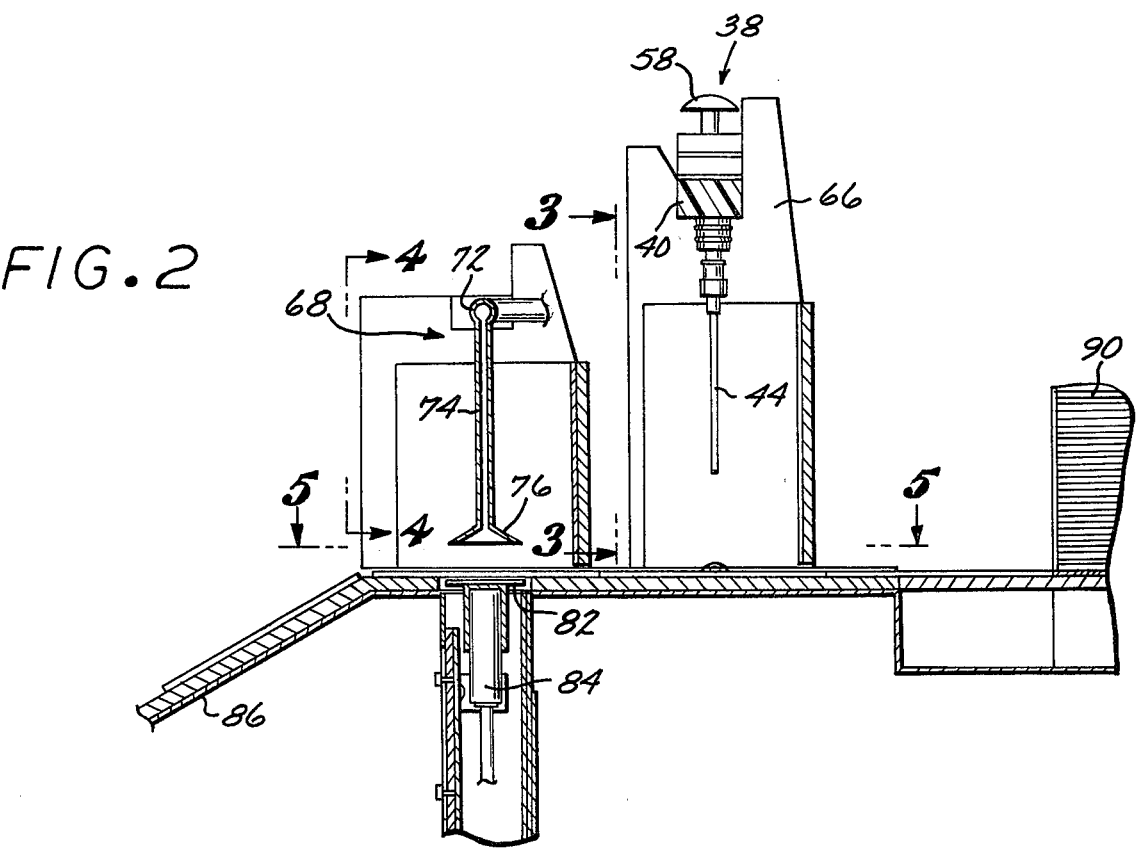
FIG. 2 is a cross-sectional view of the embodiment of FIG. 1 showing various stages of slide processing in the embodiment.
Figure 3:
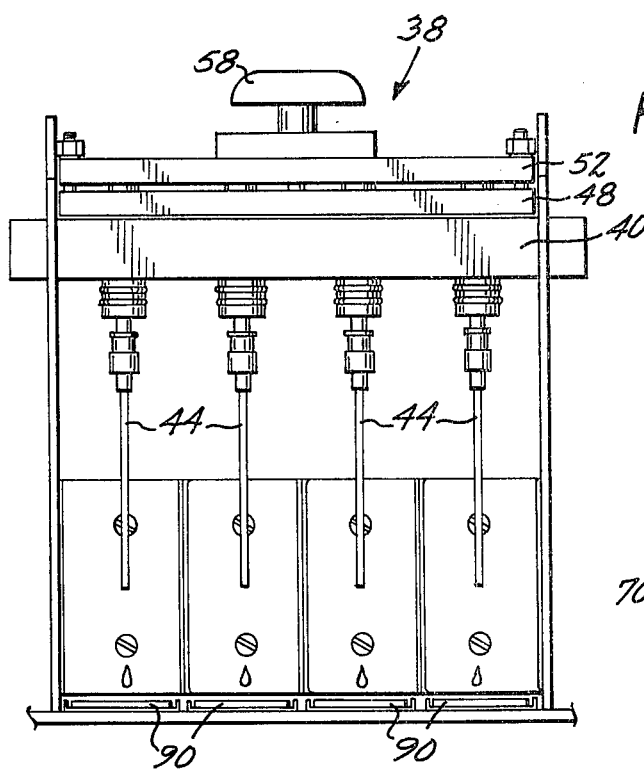
FIG. 3 is a front plan view of a cell dispenser assembly.
Figure 4:
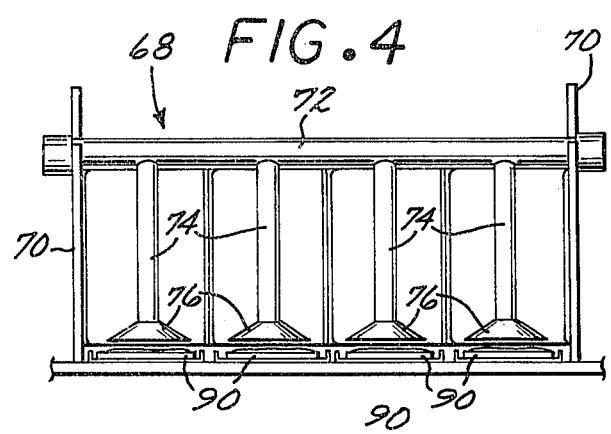
FIG. 4 is a front plan view of a cell dispersal assembly.

The slide processor device 10 has a housing 12 which contains the various components of the device 10. The rear portion of housing 12 is formed into a slide stacker compartment 14 for receiving and storing glass slides to be prepared. The slide stacker 14 is provided with a slide door 16.

A slide feeder lever 18 is connected to slide feeding mechanism 20 which is provided with bearings 22 and levers 24 together with a slide bar 26 and a stabilizer plate 28.

The housing 12 is provided with a slide plate 30 formed into channels 32 with guide pins 34. A support ledge 36 is provided for slide plate 30.

The slide processor device 10 is provided with a cell dispenser assembly 38 having a manifold element 40 provided with a plurality of sockets 42 for needles 44. An elastomeric membrane 46 located on the top of the manifold 40 is maintained in position by manifold lid 48 over the top openings 50 of sockets 42.

A plunger plate 52 is located on top of the manifold lid 48 and is provided with a plurality of fixed piston members 54 which are located over the top openings 50 of sockets 42 and the top of membrane 46.

The plunger plate 52 is maintained in position by a center guide post 56 extending through the manifold lid 48 and into manifold 40. A knob 58 is connected to the top portion of center guide post 56 and is maintained in position by knob holder 59 mounted on plunger plate 52 by screws 60.

Adjustment studs 62 and lock nuts 64 maintain the alignment of manifold 40, manifold lid 48, and plunger plate 52. Adjustment studs 62 and lock nuts 64 also provide for height adjustment of the plunger plate 52. The cell dispenser assembly 38 is supported by dispenser support frame 66 mounted on housing 12.

The slide processor 10 is provided with a cell dispersal assembly 68 having a dispersal support frame 70 mounted on housing 12 and supporting a cell dispersal manifold 72. The cell dispersal manifold 72 has a plurality of tubes 74 each terminating in a funnel shaped lower end 76. One end of the cell dispersal manifold is connected to air supply 78 which is equipped with air control valve 80.

A heating plate 82 is mounted underneath slide plate 30 and located below cell dispersal manifold 72. The heating plate 82 is provided with a variable heating element 84.

The outer end of slide plate 30 terminates in a plurality of slide chutes 86 which are postioned to drop the completed slides into slide magazines 88.

In operation, the compartment 14 of slide processor 10 is stacked with slides 90. The slide bar 26 is manually moved forward, thereby activating the feeder mechanism 20, which pushes a set of four slides 90 forward along channels 32 to a position beneath cell dispensing assembly 38. The cell dispensing assembly 38 has previously been provided with the desired cell suspension by emersing needles 44 manually into the cell suspension, pressing down plunger plate 52, and then releasing plunger plate 52. The elastomeric membrane 46 is initially depressed by pistons 54 when plunger plate 52 is pressed down manually. Upon the release of plunger plate 52, the elasticity of membrane 46 pushes pistons 54 and plunger plate 52 back to their original position and creates a suction within needles 44, thereby drawing up a pre-determined amount of cell suspension into needles 44. The amount of cell suspension drawn up can be varied by adjusting the height of plunger plate 52 through adjustment studs 62 and lock nuts 64. The greater the height, the more more suction is produced, and the greater the amount of cell suspension which will be drawn up into needles 44.

The cell dispenser assembly 38 is placed in position on dispenser support frame 66 so that each of the slides 90 is directly below each of needles 44. Plungerplate 52 is then depressed, thereby releasing a drop 92 of cell suspension on top of each of slides 90 as shown in FIG. 5.

Slide bar 26 is then manually pushed forward, thereby causing a second set of slides 90 to be pushed forward from compartment 14 to a position below cell dispenser assembly 38, which second set of slides 90 in turn pushes the first set of slides 90 having the drop 92 of cell suspension, forward to a position underneath cell dispersal assembly 68.

Figure 5:
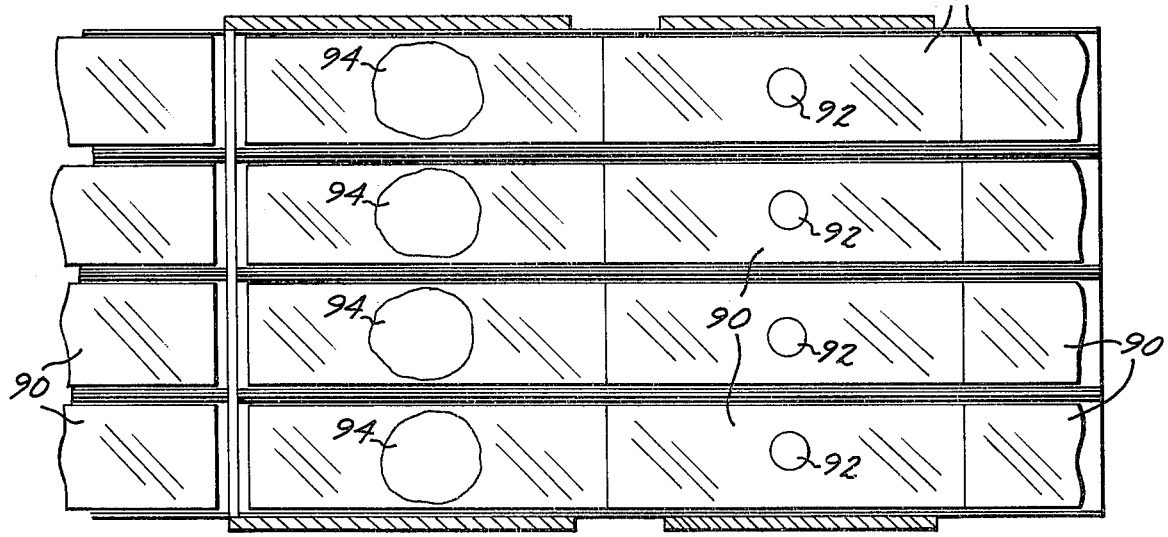
FIG. 5 is a top plan view of slides showing the spreading of the cell culture by controlled air blast.
Figure 6:
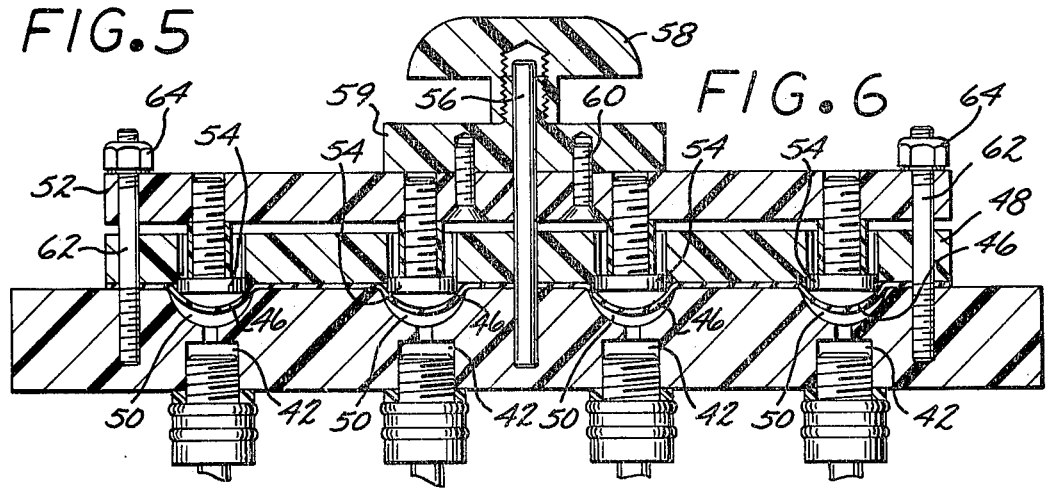
FIG. 6 is a cross-sectional view of the cell dispenser assembly of FIG. 3.
Figure 7:
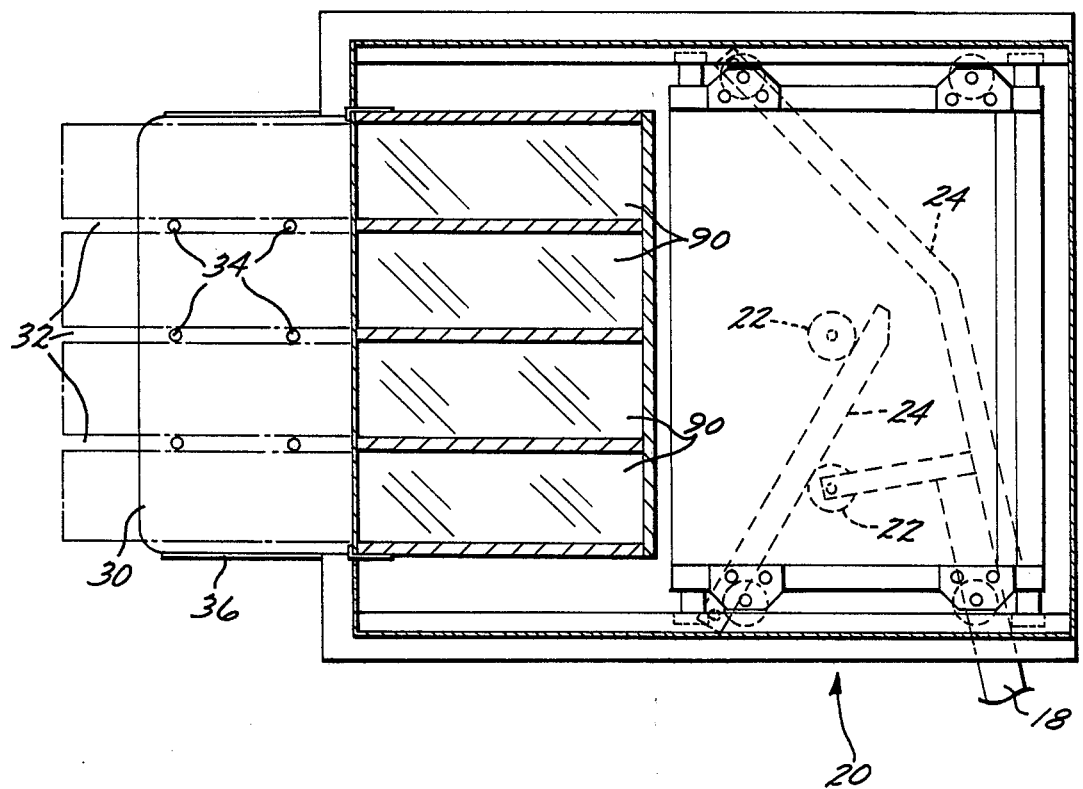
FIG. 7 is a cross-sectional view of an embodiment of the invention showing the slide channels and slide dispensing mechanism.

Air control valve 80 is then activated to provide a controlled flow of air to spread and scatter the drops 92 of cell suspension into a thin film 94 on slides 90, as shown in FIG. 5, thus dispensing with oral methods of scattering and spreading. The flow of air from air control valve 80 proceeds through tubes 74 and out of funnel shaped lower end 76 of tube 74.

Meanwhile, as if desired, heating plate 82 provides rapid drying of the film 94 in a matter of seconds.

A preferable period of time for the air flow is from one to two seconds. The heating time is preferably about 30 seconds at a temperature of 55° C. The heating time may vary from 20 to 40 seconds and the temperature may vary over a range from 50° to 90° C.

While the film 94 is drying, cell dispensing assembly 38 may be activated to deposit another drop 92 of cell suspension on each of the second set of slides 90.

After the film 94 on slides 90, the first set, has dried, the slide bar 26 is again pushed forward, thereby causing a third set of slides 90 to be pushed forward to a position underneath cell dispenser assembly 38, and also causing the second set of slides 90 to be pushed forward to a position underneath cell dispensing assembly 66, and in turn causing the first set of slides 90 to slide down slide chutes 86 into slide magazines 88.

In this manner, the slide processor device 10 will produce finished slides in a fraction of a time usually required by conventional manual methods. The various component parts of slide processor 10 may be made of any suitable material. Although I have described my invention in detail with reference to the accompanying drawings illustrating preferred forms of my invention, it is understood that numerous changes in the details of construction and arrangement of parts may be made without departing from the spirit and scope of the invention as hereinafter claimed.

I claim:

1. A semi-automated slide processor device for preparing simultaneously a plurality of slides of cell cultures for cytogenetic analysis, comprising:

stacking means for stacking a supply of slides; including a plurality of stacks of said slides;

cell dispensing means for releasing a suspension of cells simultaneously on each of a plurality of slides, said cell dispensing means including a manifold means having a plurality of openings covered by an elastomeric membrane, and including plunger means for producing pressure on said manifold means to release said suspension of cells;

cell dispersal means for spreading a suspension of cells into a film on each of said slides simultaneously; and means for moving slides from said stacking means to a location beneath said cell dispensing means and then to a location beneath said cell despersal means, said means for moving slides including a plurality of longitudinal channels for passage of slides.

2. A semi-automated slide processor device according to claim 1 in which said device has a heating means for drying said film on said slides.

3. A semi-automated slide processor device according to claim 1 in which said device has collecting means for collecting the resulting slides.

4. A semi-automated slide processor device for preparing simultaneously a plurality of slides of cell cultures for cytogenetic analysis, comprising:

a housing having a compartment for stacking slides, said compartment including a plurality of stacks of said slides;

a plurality of longitudinal channels for passage of slides located at the bottom of said housing, each of said longitudinal channels terminating in a slide chute;

a slide feeding assembly having bearings and lever arms arranged to push a plurality of slides simultaneously from said compartment onto said longitudinal channels;

a removable cell dispensing assembly having a manifold with openings adapted to receive needles, a manifold lid, an elastomeric membrane placed between said manifold and said manifold lid, and a plunger plate member having a plurality of fixed pistons, said pistons corresponding to said openings and contacting said elastomeric membrane; and a cell dispersal manifold having a plurality of tube members with funnel shaped lower ends.

5. A semi-automated slide processor device according to claim 4 in which said device has means for heating said slides after passing by said cell dispensing assembly.

6. A semi-automated slide processor device according to claim 4 in which said device has collecting means for the resulting slides, said collecting means adjoining said slide chutes.

* * * * *